US009662676B2

(12) United States Patent
Kayser

(10) Patent No.: US 9,662,676 B2
(45) Date of Patent: May 30, 2017

(54) LUER-CONNECTOR WITH RETAINING SCREW FOR ATTACHMENT TO AN ADMINISTRATION DEVICE

(75) Inventor: Ralph Egon Kayser, Luzern (CH)

(73) Assignee: MEDMIX SYSTEMS AG, Rotkreuz (CH)

( * ) Notice: Subject to any disclaimer, the term of this patent is extended or adjusted under 35 U.S.C. 154(b) by 248 days.

(21) Appl. No.: 13/635,741

(22) PCT Filed: Mar. 22, 2011

(86) PCT No.: PCT/CH2011/000057
§ 371 (c)(1),
(2), (4) Date: Sep. 18, 2012

(87) PCT Pub. No.: WO2011/116484
PCT Pub. Date: Sep. 29, 2011

(65) Prior Publication Data
US 2013/0023833 A1    Jan. 24, 2013

(30) Foreign Application Priority Data

Mar. 26, 2010 (CH) ...................................... 0446/10

(51) Int. Cl.
| | | |
|---|---|---|
| *B05C 17/005* | (2006.01) | |
| *A61M 5/19* | (2006.01) | |
| *A61B 17/00* | (2006.01) | |
| *A61C 8/00* | (2006.01) | |
| *A61M 5/34* | (2006.01) | |
| *A61M 39/10* | (2006.01) | |

(52) U.S. Cl.
CPC ......... *B05C 17/00553* (2013.01); *A61M 5/19* (2013.01); *B05C 17/00513* (2013.01);
(Continued)

(58) Field of Classification Search
CPC .............. A61M 3/005; A61M 5/16827; A61M 5/1407; A61M 5/2006; A61M 2005/2451;
(Continued)

(56) References Cited

U.S. PATENT DOCUMENTS 4,243,034 A * 1/1981 Brandt ..................... 604/167.01
4,629,455 A   12/1986 Kanno
(Continued)

FOREIGN PATENT DOCUMENTS

DE     86 10 008 U1    8/1986
DE     37 37 665 A1    5/1989
(Continued)

OTHER PUBLICATIONS

International Search Report of PCT/CH2011/000057 dated Jun. 29, 2011.

*Primary Examiner* — Imani Hayman
*Assistant Examiner* — Nilay Shah
(74) *Attorney, Agent, or Firm* — Sughrue Mion, PLLC

(57) ABSTRACT

An attachment part with a coupling part by means of which coupling part the attachment part can be attached to a dispensing unit. The coupling part has a female cone area, with a continuous inlet opening, and a locking structure arranged around the female cone area. The female cone area can be pushed onto a male cone area of the dispensing unit, in order thereby to connect the attachment part to the dispensing unit. The locking structure serves to secure the attachment part on the dispensing unit. The first coupling part additionally has a rotation element, which is rotatable concentrically about the female cone area and on which the first locking structure is formed. The rotation element has an actuating element, which serves to rotate the rotation element relative to the female cone area.

17 Claims, 4 Drawing Sheets

(52) U.S. Cl.
CPC ... *A61B 2017/00495* (2013.01); *A61C 8/0089* (2013.01); *A61M 5/347* (2013.01); *A61M 2039/1033* (2013.01); *A61M 2039/1038* (2013.01); *A61M 2039/1077* (2013.01); *A61M 2039/1083* (2013.01); *A61M 2039/1088* (2013.01)

(58) Field of Classification Search
CPC ............... A61M 5/31; A61M 5/31596; A61M 2039/1033; A61M 2039/1088; A61M 2039/1083; A61M 39/10
USPC ... 604/232, 82, 85, 191, 240, 218, 241, 187, 604/242, 243, 533–535
See application file for complete search history.

(56) References Cited

U.S. PATENT DOCUMENTS

| | | | |
|---|---|---|---|
| 4,979,942 A * | 12/1990 | Wolf et al. | 604/83 |
| 5,489,274 A * | 2/1996 | Chu et al. | 604/167.05 |
| 5,702,374 A | 12/1997 | Johnson | |
| 5,984,373 A | 11/1999 | Fitoussi et al. | |
| 7,118,560 B2 * | 10/2006 | Bonaldo | 604/537 |
| 2006/0033334 A1 | 2/2006 | Weber et al. | |
| 2006/0157984 A1 | 7/2006 | Rome et al. | |
| 2007/0088293 A1 * | 4/2007 | Fangrow | A61M 39/10 604/246 |
| 2007/0129705 A1 | 6/2007 | Trombley, III et al. | |

FOREIGN PATENT DOCUMENTS

| | | |
|---|---|---|
| DE | 20 2004 012 714 U1 | 12/2004 |
| EP | 0 775 501 A1 | 5/1997 |
| EP | 0 953 365 A2 | 11/1999 |
| EP | 953365 A2 * | 11/1999 |
| EP | 1 552 858 A1 | 7/2005 |
| WO | 2009/093249 A1 | 7/2009 |
| WO | 2010/009563 A1 | 1/2010 |
| WO | 2010/020061 A1 | 2/2010 |
| WO | 2010/061234 A1 | 6/2010 |

\* cited by examiner

LUER-CONNECTOR WITH RETAINING SCREW FOR ATTACHMENT TO AN ADMINISTRATION DEVICE

CROSS REFERENCE TO RELATED APPLICATIONS

This application is a National Stage of International Application No. PCT/CH2011/000057 filed Mar. 22, 2011, claiming priority based on German Patent Application No. 00446/10 filed Mar. 26, 2010, the contents of all of which are incorporated herein by reference in their entirety.

TECHNICAL FIELD

The present invention relates to an attachment part for attachment to a dispensing unit. The attachment part has at least one coupling part, by means of which the attachment part can be attached to a dispensing unit. The coupling part comprises a conical connecting region and a locking structure.

PRIOR ART

Dispensing units, such as for example syringes for the administering of medicaments to patients, have been generally known for a long time and are often used in medicine. A commercially available syringe has a syringe housing with a distal delivery opening and a piston, which is able to be pushed in from a proximal end into a reservoir of the syringe housing. The reservoir serves here to receive a fluid product, for example a medicament. An attachment part, such as for example an injection cannula or a connecting tube, is able to be attached to the delivery opening. In the region of the delivery opening, for that purpose, generally a coupling part is formed, which serves for the attachment of various kinds of attachment parts. The so-called luer connection has become established in medicine for the connecting of attachment parts and syringes. One of the parts which is to be connected, usually the syringe, has here a male cone area and the other part has a female cone area formed in a complementary manner thereto. The female cone area of the attachment part is then able to be pushed onto the male cone area of the syringe, whereby a fluid-tight connection is produced between the reservoir of the syringe and the interior of the attachment part. To secure the attachment part on the syringe, the coupling part often has in addition a securing sleeve with an internal thread, into which an external thread is able to be screwed, which is placed on the attachment part around the female cone area.

The cones of such luer closures usually have a gradient of 6%. Luer closures are described in detail in the Standards DIN EN 1707:1996 and DIN EN 20594-1:1993 and are standardized accordingly.

When the securing sleeve is rigidly connected with the syringe housing, this entails a reciprocal rotation of the two cone areas which are to be connected. This is a problem for example in the case of a double piston syringe, in which the syringe housing has two separate reservoirs with respectively a delivery opening and a coupling part. An attachment part with two coupling parts constructed in a complementary manner thereto is then not able to be attached to the double piston syringe, because the two cone areas of the double piston syringe are connected rigidly with one another. A simpler securing of the luer connection is enabled when the securing sleeve is mounted rotatably on the male cone, because then the two parts which are to be connected do not have to be rotated with respect to one another during the screwing together of the two threads. The documents U.S. Pat. Nos. 4,629,455 and 5,702,374 describe such devices, in which the securing sleeve is mounted respectively rotatably on the male cone.

The document DE 37 37 665 describes a luer closure in which the entire coupling part with the male luer cone and with the securing sleeve are mounted rotatably on a tube which is to be connected. A reciprocal rotating of the male and of the female cone area is, however, disadvantageous, because in so doing a friction force occurs between the two conical areas, which makes the screwing together of the two coupling parts difficult for the user. A close-fitting screwing together of the two threads is, however, desired, because in so doing the two coupling parts which are to be connected press onto one another in an intensified manner and thereby the sealing effect of the connection is improved.

Further luer closures are described on the documents U.S. Pat. No. 5,984,373, WO 2009/093249, US 2006/0157984 and DE 86 10 008.

Often, however, it is desirable to produce attachment parts which are able to be attached in as simple a manner as possible to already existing syringes or other dispensing units, such as for example double or multiple piston syringes or else cartridges. As in many of these dispensing units the securing sleeve is not, however, rotatable, it is furthermore necessary that the attachment part has to be rotated as a whole with respect to the dispensing unit on screwing together the two threads, when the coupling part of the attachment part is constructed according to the prior art. Depending on the function and configuration of the attachment part, this can constitute a considerable disadvantage or even make the attachment to such a dispensing unit impossible.

In the documents US 2007/0129705, EP 0 775 501, EP 0 953 365 and EP 1 552 858 attachment elements are disclosed in which respectively a locking element is mounted around a luer cone. The locking element is arranged here respectively rotatably to the luer cone and has a locking structure in order to lock reciprocally the attachment element and a counter-part attached thereon.

SUMMARY OF THE INVENTION

It is an object of the present invention to provide an attachment part which has a female cone area for connection with a dispensing unit, and which can be secured on a dispensing unit with a securing sleeve such that the attachment part does not have to be rotated as a whole with respect to the dispensing unit, even when the dispensing unit has a torque-proof securing sleeve. The attachment part is, in addition, to have a simple handling and as simple a construction as possible.

The present invention therefore makes available an attachment part with at least a first coupling part, by means of which the attachment part is able to be attached to a dispensing unit, in particular a medical dispensing unit, the first coupling part having a female cone area, which has an inlet opening going throughout the female cone area, and which is able to be pushed along a pushing-on direction onto a male cone area of the dispensing unit, in order to thereby connect the attachment part with the dispensing unit; and a first locking structure, which is arranged in a region surrounding the female cone area and serves for securing the attachment part to the dispensing unit.

The first coupling part has here a rotation element which is rotatable concentrically about the female cone area and on which the first locking structure is formed. The rotation element has in addition an actuation element which serves to rotate the rotation element relative to the female cone area, even when the dispensing unit has a torque-proof securing sleeve.

Such a configuration of the attachment part permits the attachment part to be connected to the dispensing unit and to be secured thereon, without the attachment part having to be rotated with respect to the dispending unit, even when the dispensing unit has a torque-proof securing sleeve.

A female cone area is understood to mean an area which has a conically constructed inner surface, and a male cone area is understood to mean an area which has a conically constructed outer surface. Whereas the inner surface of the female cone area widens in the pushing-on direction, the outer surface of the male cone area narrows in an opposite direction to the pushing-on direction. The female or respectively male cone area defines here a longitudinal axis which extends centrally with respect to this inner or respectively outer surface. The rotation element is preferably rotatable about this longitudinal axis of the female cone area.

The attachment part can be constructed to fulfil the most varied of functions in accordance with the prior art. In particular, the attachment part can be constructed as an adapter which enables the attaching of any desired accessories, such as for example mixing attachments, injection cannulas and connection tubes, to the dispensing unit. The attaching of an attachment part to the dispensing unit or of an accessory to the attachment part respectively means such an attaching in which the two parts concerned are not only fixed to one another, but also cooperate functionally. Such a cooperation is realized in particular in that a fluid duct, which is constructed in one part, opens out into a fluid duct existing in the other part.

The dispensing unit can be, in particular, a commercially available syringe for the administering of a medicament to patients, i.e. a single-piston syringe.

In a preferred embodiment, the attachment part has at least two first coupling parts arranged parallel to one another. A parallel arrangement of the first coupling parts means such an arrangement in which the female cone areas of the coupling parts are arranged parallel to one another, wherein in particular the longitudinal axes of these cone areas extend parallel to one another. The attachment part is thereby able to be attached to a plurality of dispensing units, in particular to several single-piston syringes, or to a multiple-piston syringe, in particular to a double-piston syringe, or respectively to a cartridge with several reservoirs and corresponding coupling parts. Such a multiple-piston syringe or respectively cartridge has several reservoirs with corresponding delivery openings. The products contained in the various reservoirs are able to be ejected individually by individual pistons or jointly by means of a multiple piston through the various delivery openings. In the case of a multiple piston, the pistons are connected with one another for this at their proximal ends. Advantageously, the first coupling parts are each constructed in a similar manner. They can, however, also be constructed differently and have a coding, in order to only permit the attaching of particular dispensing units to respectively a first coupling part in question.

In a preferred embodiment, the attachment part is constructed as an attachment adapter which serves for the attaching of further accessories to the dispensing unit. Such an attachment adapter can enable for example the connecting of various attachment systems. An accessory with a proprietary coupling part of a first attachment system is then able to be attached by means of the attachment adapter to the dispensing unit, which has a proprietary coupling part according to a second attachment system. Preferably, the attachment part therefore has an outlet opening which is in fluid-communicating connection with the inlet opening, and has an attachment structure which is suited to attaching an accessory on the attachment part such that the outlet opening opens out in a fluid-tight manner into an opposite fluid duct of the accessory. The accessory can be, for example, a mixing attachment, an injection cannula, a spray nozzle, a closure part, a connecting tube, another syringe or dispensing unit, or else an accessory which permits the attaching of still further attachment elements. The attachment structure can be constructed for example to undergo a screw connection, a bayonet connection or a snap connection with the accessory.

Preferably, the female cone area forms a luer cone, i.e. a standardized cone with a gradient of 6%.

Preferably, the first locking structure is arranged on the radial outer side of the rotation element and in particular is constructed as an external thread. Such a configuration of the locking structure can in particular bring it about that on securing of the attachment part on the dispensing unit, the female cone area of the attachment part is moved towards the male cone area of the dispensing unit and is pressed on the latter. The connection between attachment part and dispensing unit, and in particular the sealing effect of this connection, can be thereby improved. Alternatively, instead of an external thread, two lugs lying radially opposite can be provided for example as first locking structure, which engage into a thread structure or into guide grooves of the securing sleeve of the dispensing unit.

For the applying of the rotation element, a shoulder is constructed, having a stop surface, in the region of the female cone area, which stop surface points in a substantially opposite direction to the pushing-on direction. The shoulder is preferably constructed so as to be circumferential. The region of the female cone area comprises here the outer surface of the female cone area which extends radially around the conical inner surface which widens in the pushing-on direction, and the outer surface of a possible attachment tube, which extends directly from the female cone area away in the direction pointing contrary to the pushing-on direction. The rotation element has one or more, preferably precisely two behind-engaging elements, which themselves respectively likewise have a stop surface, by which they abut against this stop surface arranged in the region of the female cone area, such that a further movement of the rotation element in the pushing-on direction is prevented. Preferably, respectively two of the behind-engaging elements of a rotation element form a pair lying diametrically opposite. In order to facilitate the assembly, the behind-engaging elements are constructed so as to be flexible and advantageously have respectively a free end. At the free end respectively an oblique surface is preferably constructed here, which is inclined with respect to the longitudinal axis of the female cone area. Preferably, the oblique surface is inclined here such that it moves away from the longitudinal axis of the female cone area in the direction pointing contrary to the pushing-on direction.

The rotation element is preferably freely rotatable. This means that the rotation element is rotatable about an angle range of at least 360°.

The rotation element preferably has a rotation sleeve which surrounds the female cone area substantially circumferentially and at the outer side of which the locking structure is constructed. The actuating element is, in addition, preferably constructed as a rotation ring which is mounted on the rotation sleeve. The rotation ring advantageously has here a greater outside radius than the rotation sleeve, whereby it is better accessible for the user. If behind-engaging elements are present, these are advantageously arranged radially in the interior of the rotation ring.

In addition, a dispensing device, in particular a medical dispensing device, is indicated, which has an attachment part according to the invention and a dispensing unit. The dispensing unit has here a housing with at least one reservoir; and at least a second coupling part with a securing sleeve and with a male cone area which is arranged radially at a distance within the securing sleeve and has a delivery opening, which goes throughout the male cone area, and which is in fluid-communicating connection with the reservoir.

The female cone area of the attachment part is able to be pushed here onto the male cone area of the dispensing unit, so that the reservoir is in fluid-communicating connection with the inlet opening. In addition, the securing sleeve has a second locking structure, which is able to be locked with the first locking structure such that the attachment part is secured on the dispensing unit.

The second coupling part is therefore constructed in a complementary manner to the first coupling part of the attachment part.

The securing sleeve can be mounted rotatably on the housing or, as is preferred here, can be mounted in a torque-proof manner on the housing. The second locking structure is generally arranged internally on the securing sleeve and is preferably constructed as an internal thread. The second locking structure can, however, also be configured for example as a guide path in the form of a depression on the inner side of the securing sleeve or in the form of a continuous slit in the securing sleeve.

The dispensing unit can be constructed as a single-piston syringe or as a double- or multiple-piston syringe or as a cartridge. In this case, the dispensing unit can have two or more second coupling parts arranged parallel to one another, which are then able to be coupled and locked with at least two first coupling parts of the attachment part which are arranged parallel to one another.

In a preferred embodiment, the double- or multiple-piston syringe has two or more single-piston syringes which are detachable from one another and able to be used separately from one another. The single-piston syringes can be connected with one another here for example so as to be detachable at their proximal ends by means of a connecting element. In particular, commercially available standard syringes are able to be used here, whereby multiple-piston syringes are able to be produced in a very favourably priced manner. Through the fact that the single-piston syringes respectively do not have to be rotated as a whole relative to the attachment part, outwardly projecting elements of the syringes do not get in the way on the attaching of the syringes to the attachment part. The syringes can therefore be arranged closer to one another. The space requirement of the dispensing device is therefore distinctly reduced. If the attachment part for example is constructed as a mixing element or as an adapter for the attaching of a mixing attachment or of another accessory, owing to the closer arrangement of the syringes, fluid ducts present in the attachment part have a shortened length in total. A loss volume of the fluid product which remains in the attachment part after the dispensing is thereby distinctly reduced.

The dispensing device can have in addition a mixing attachment with a second attachment structure and with a mixing chamber, wherein the mixing attachment is able to be attached to the attachment part by connecting the first attachment structure with the second attachment structure such that the outlet openings of the attachment part are respectively in fluid-communicating connection respectively with the mixing chamber.

BRIEF DESCRIPTION OF THE DRAWINGS

Preferred embodiments of the invention are described below with the aid of the drawings, which serve only for explanation and are not to be construed as being limiting. In the drawings there are shown.

DESCRIPTION OF PREFERRED EMBODIMENTS

Figure 1:
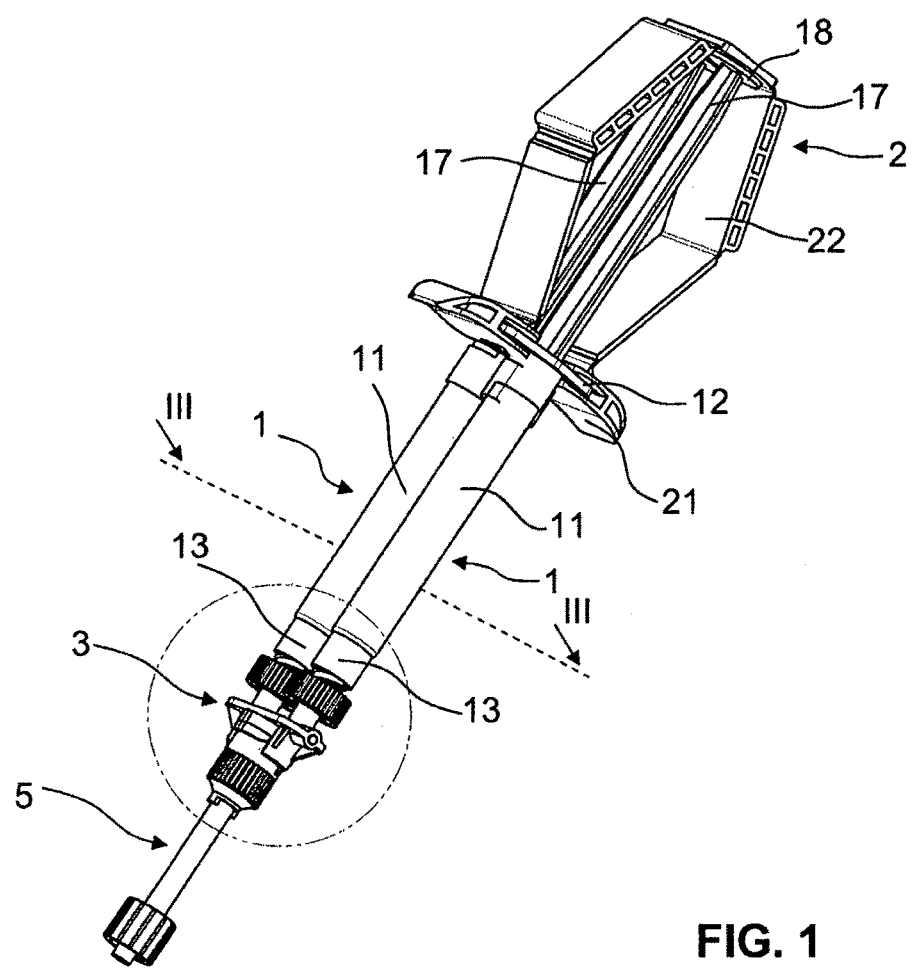
FIG. 1 a perspective view of a dispensing device with an attachment part according to the invention and with a dispensing unit according to a first embodiment.
Figure 2:
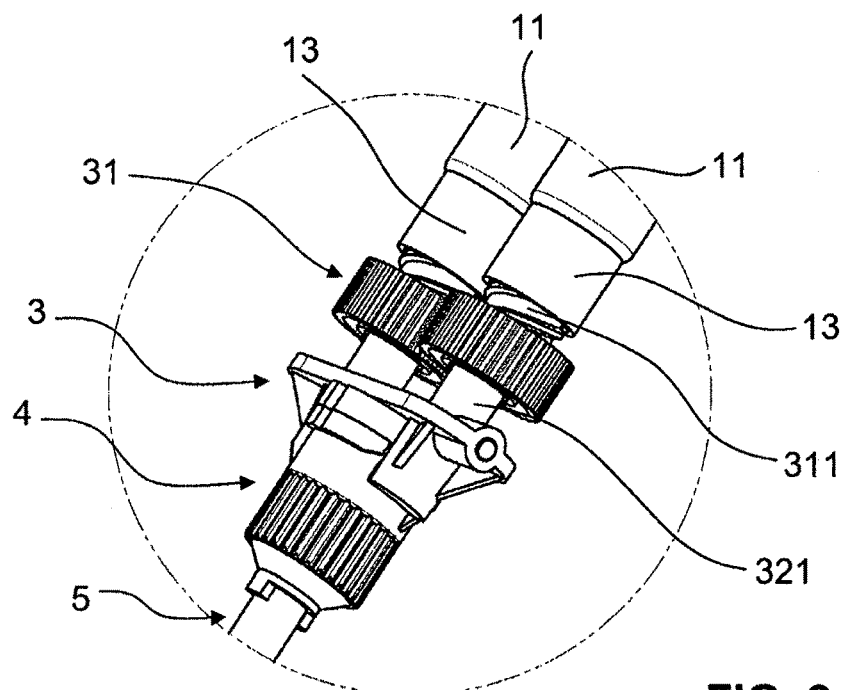
FIG. 2 a perspective detail view of the region of the dispensing device marked in FIG. 1.

FIGS. 1 to 4 show a medical dispensing device with an attachment part 3 according to the invention in accordance with a first embodiment. The attachment part 3 is constructed here as an attachment adapter. The dispensing device has a dispensing unit in the form of two syringes 1, which are connected with one another respectively at a distal housing end via an attachment part 3. At their proximal end, the two syringes 1 are connected detachably with one another via a syringe holder 2. On the side of the attachment part 3 lying opposite the syringes 1, a mixing attachment 5 is attached to the attachment part 3 and is secured thereon by means of a connecting sleeve 4.

In the present embodiment, the syringes 1 are respectively commercially available syringes with a housing which has a distal delivery opening 15 and a proximal opening for the pushing in of a piston 17. The housing has a reservoir 16, which serves to receive a fluid medicinal product and is delimited in a radial direction by a hollow cylindrical side wall 11. By pushing the piston 17 forward into the reservoir 16, the fluid product is able to be ejected in distal direction through the delivery opening 15. A sealing element 19, constructed at the distal end of the piston 17, serves here to prevent an escape in the proximal direction of the fluid product which is stored in the reservoir 16. In order to facilitate the pushing forward of the piston 17 into the reservoir 16, a pressure plate 18 is constructed at the proximal end of the piston 17. In addition, the syringe housing has holding wings 12 which are mounted at the proximal end of the side wall 11. The holding wings 12 project here outwards from the housing in two diametrically opposite directions and serve to offer to the user a contact surface for the fingers, pointing in the distal direction, whilst the piston 17 is pushed forward by thumb pressure on the pressure plate 18. In the region of the delivery opening 15, a coupling part is constructed on the syringe 1, which coupling part permits an applying of any desired accessories to the syringe 1, such as for example injection cannulas, spray nozzles, closures, connecting tubes etc.

The coupling part of the syringe 1 has a male cone area in the form of a luer cone 14. The male luer cone 14, which delimits the delivery opening 15, narrows on its outer side in a direction pointing away from the reservoir 16. A securing sleeve 13, around the male luer cone 14 and spaced apart therefrom, is mounted securely on the syringe housing. The securing sleeve 13 has on its inner side a locking structure in the form of an internal thread.

In the present embodiment, the two syringes 1 are connected detachably with one another respectively at their proximal housing end, in the region of the holding wings 12, by means of a syringe holder 2. The syringe holder 2 has a connecting element 21 for this, which receives the holding wings 12 such that the holding wings 12, lying diametrically opposite one another, of the one syringe 1 are arranged parallel to those of the other syringe 1. The syringe holder 2 has, in addition, an actuating element 22, through which the pistons 17 of the two syringes 1 are able to be pushed forward together. The syringe holder 2 is described in detail in particular in WO 2010/009563 on page 2, line 22 to page 4, line 17, to which reference is to be made here expressly.

Figures 3, 4:
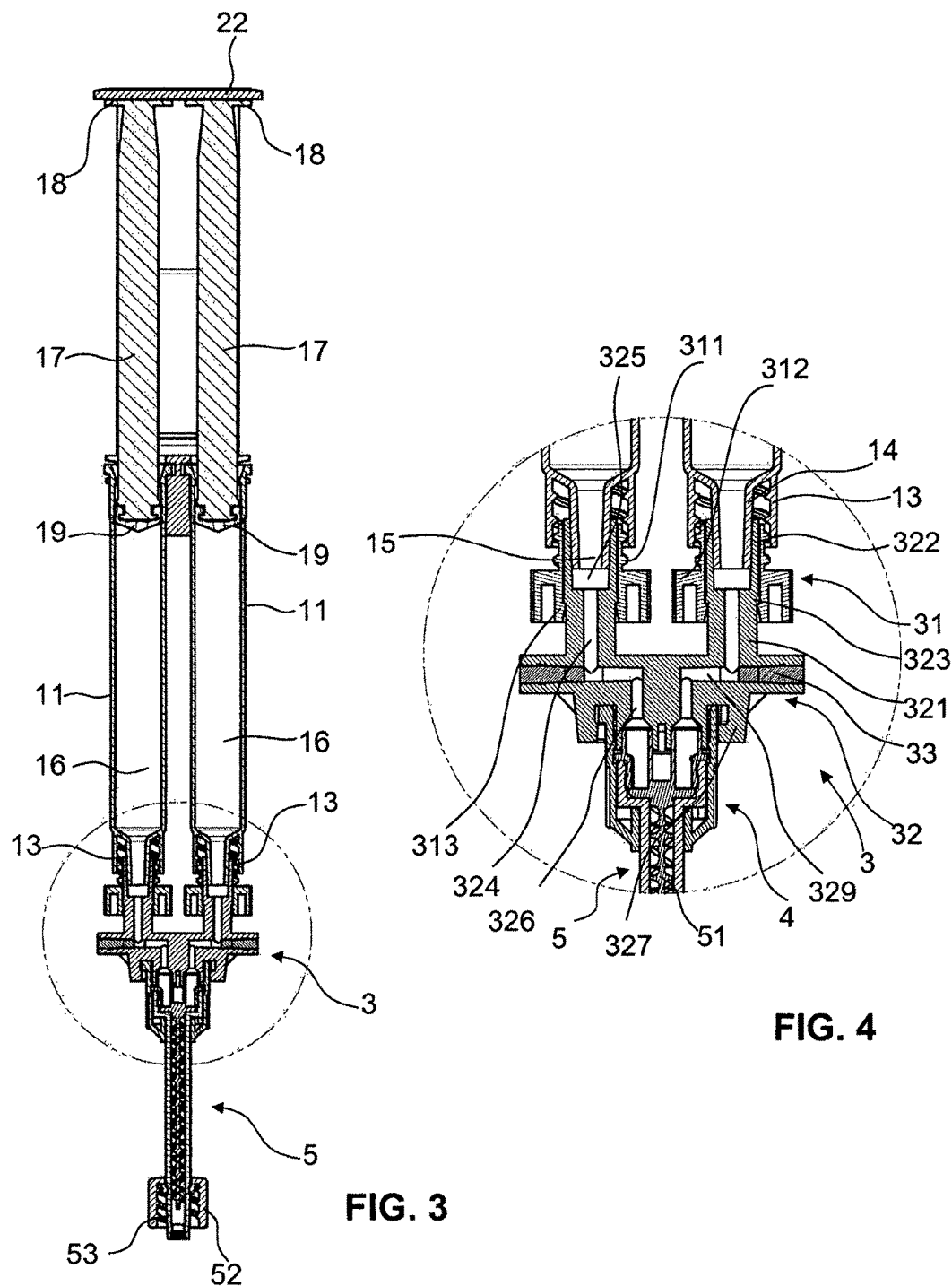
FIG. 3 a central sectional view in the plane of the dispensing device shown in FIG. 1.
FIG. 4 a detail sectional view of the region of the dispensing device marked in FIG. 3.
Figure 5:
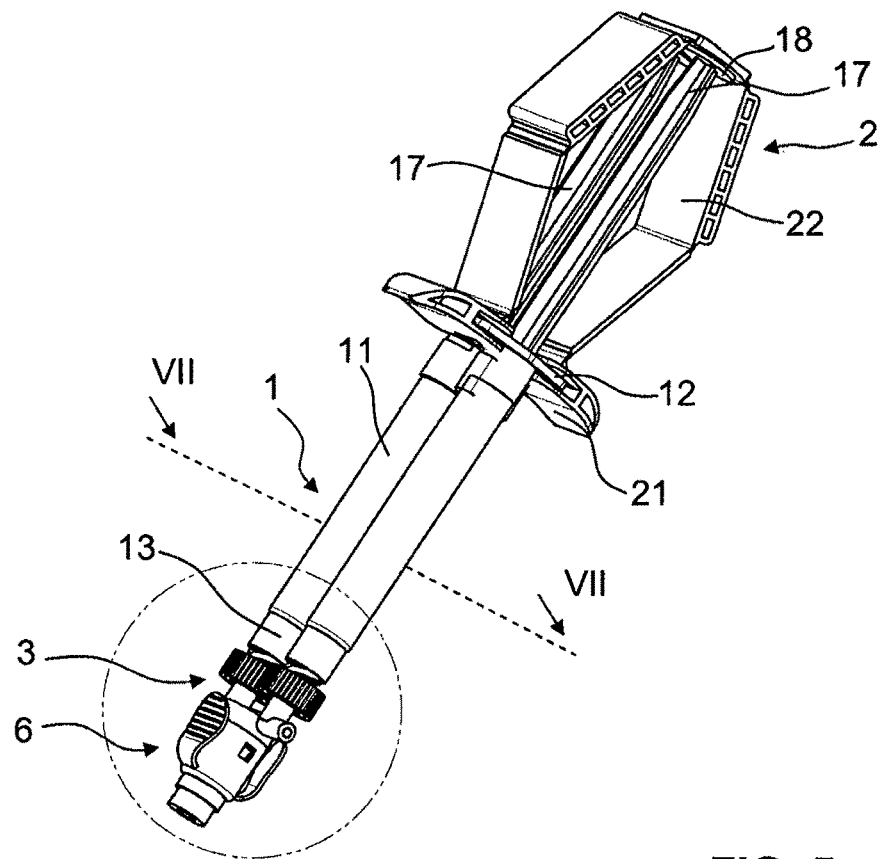
FIG. 5 a perspective view of a dispensing device with an attachment part according to the invention and with a dispensing unit according to a second embodiment.
Figure 6:
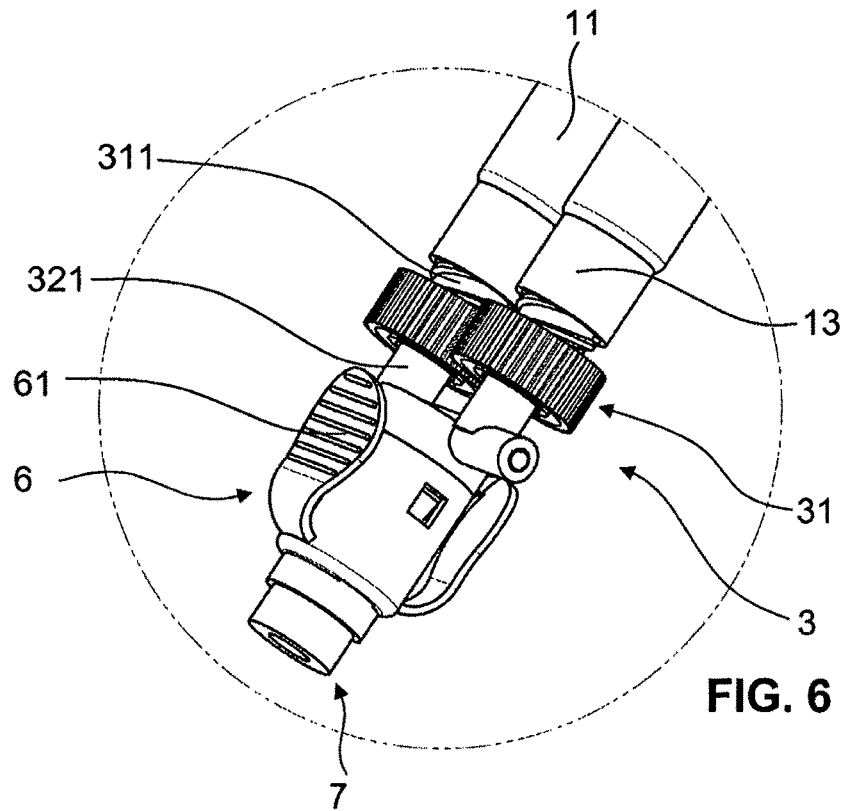
FIG. 6 a detail view of the region of the dispensing device marked in FIG. 5.
Figures 7, 8:
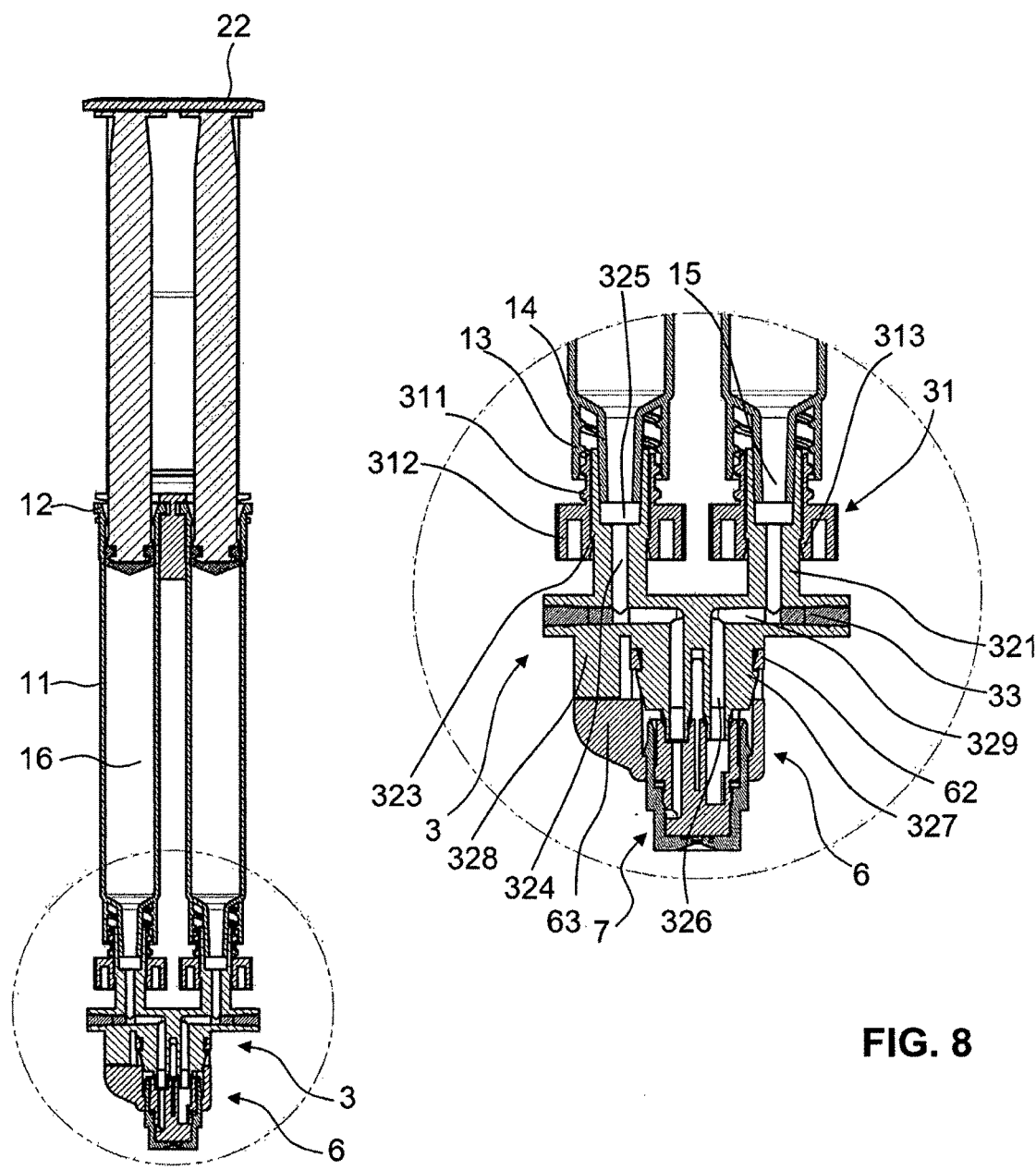
FIG. 7 a central sectional view in the plane VII-VII of the dispensing device shown in FIG. 5.
FIG. 8 a detail sectional view of the region of the dispensing device marked in FIG. 7.

The attachment part 3, which is shown in detail in particular in FIG. 4, has in the present embodiment a housing 32, on which two rotation elements 31 are mounted. The two rotation elements 31 belong to respectively one of a total of two coupling parts present on the attachment part 3, which are constructed identically to one another. Each of the coupling parts serves to connect the attachment part 3 with respectively a syringe 1 and to secure it thereon. The two coupling parts extend parallel to one another here and have respectively a female cone area 322 with a continuous inlet opening 325. The female cone area 322 here is a female luer cone which is suited to be pushed along a pushing-on direction onto the male luer cone 14 constructed on the syringe 1, in order to thereby produce a connection between the attachment part 3 and the syringe 1. The syringe 1 and the attachment part 3 are then connected with one another such that the delivery opening 15 of the syringe 1 opens out towards the exterior in a fluid-tight manner into the inlet opening 325 of the attachment part 3. The inlet opening 325 widens for this towards the pushing-on direction. In the opposite direction to the pushing-on direction, the female luer cone 322 continues into an attachment tube 321. The attachment tube 321 has a longitudinal opening 324, into which the inlet opening 325 opens. The longitudinal opening forms here a fluid duct. The attachment tube 321 has a thicker wall thickness than the luer cone 322. In the transition region between inlet opening 325 and fluid duct 324, a circumferential shoulder 323 is therefore constructed on an inner side of the housing 32. In addition, a circumferential shoulder 323 is constructed on the outer side of the attachment tube 321 in the region of the female cone area 322. The shoulder 323 has, in particular, a stop surface which points in a direction oppositely directed to the pushing-on direction.

The coupling parts of the attachment part 3 have, in addition, respectively a freely rotatable rotation element 31. The rotation element 31 comprises inter alia a threaded sleeve 311, which is dimensioned such that its inside radius is slightly greater than the outside radius of the female luer cone 322. A locking structure in the form of an external thread is constructed on the radial outer side of the threaded sleeve 311. This external thread is therefore arranged around the female luer cone 322.

A rotation ring 312 is mounted at the distal end of the threaded sleeve 311 over a connecting region extending outwards perpendicularly in radial direction. The rotation ring 312 has here a substantially greater outside radius than the threaded sleeve 311. In the radial inner region of the rotation ring 312, behind-engaging elements 313 are constructed, which extend respectively in distal direction and have a stop surface pointing in proximal direction. The behind-engaging elements 313 extend here equally far in the distal direction as the rotation ring 312. The shoulder 323, constructed on the housing 32, serves as an element cooperating with the behind-engaging elements 313. Owing to the stop of the behind-engaging elements 313 on the stop surface of the shoulder 323 pointing in distal direction, the shoulder 323 delimits a movement of the rotation element 31 relative to the female conical area 322 in the proximal direction. The rotation element 31 is, however, arranged so as to be freely rotatable, i.e. about an angle range of at least 360°, around the female luer cone 322. The engaging-behind elements 313 are constructed so as to be flexible in this embodiment, in order to enable a facilitated mounting of the rotation elements 31 on the housing 32 during installation.

The rotation elements 31 serve as a whole respectively to secure the attachment part 3, connected with the syringes 1 via the cone areas 322 and 14, to the coupling parts of the syringes 1. For this, the external thread of the threaded sleeve 311 is screwed into the internal thread of the securing sleeve 13, without the adapter housing 32 having to be rotated with respect to the syringe housing. Through the fact that it is not necessary to rotate the two syringe housings with respect to the adapter housing 32, a much simpler mounting of the two syringe housings on the attachment part and a closer arrangement of the two syringes 1 is made possible. If the attachment part 3 were to have coupling parts according to the prior art, the syringes would have to be screwed in as a whole respectively into the attachment part 3, which would only be possible with a sufficiently great spacing of the two syringes 1 such that the holding wings 12 do not abut one another reciprocally.

The rotation ring 312 guarantees for the user the accessibility of the rotation element 31. On screwing in the rotation element 31 into the securing sleeve 13, the male luer cone 14 is pushed further into the female luer cone 322. Owing to the conical shapes of the luer cones 14 and 322, the female luer cone 322 is pressed increasingly against the male luer cone 14 during the screwing in of the threaded sleeve 311. The fluid-tight connection between the male luer cone 14 and the female luer cone 322 is thereby improved on screwing the rotation element 31 into the securing sleeve 13. In addition, the screwing serves for the mechanical securing of the luer connection.

The two parallel attachment tubes 321 and the fluid ducts 324, delimited thereby, of the housing 32 extend respectively parallel to one another in the distal direction. The fluid ducts 324 open at their distal end respectively into a transverse duct 329. These two transverse ducts 329 extend here in a direction perpendicular to the fluid ducts 324 such that they move close to one another. The side openings of the transverse ducts 329, being present due to the manufacturing process, facing away from one another, are closed respectively in a fluid-tight manner by a plug 33. The transverse ducts 329 open then respectively into attachment ducts, respectively perpendicular thereto, extending in the distal direction, which attachment ducts finally open into distal outlet openings 326. The two outlet openings 326 are therefore arranged closer to one another than the inlet openings 325.

In the region of the outlet openings 326 an attachment structure 327 is constructed, which serves for the attaching of the most varied of accessories. Such an accessory can be, for example, a mixing attachment 5. The latter is secured, as shown in FIG. 4, via a connecting sleeve 4 by means of a bayonet closure on the attachment structure 327 of the attachment part 3. The outlet openings 326 of the attachment part 3 open here into corresponding, opposite inlet channels of the mixing attachment 5. These inlet channels of the mixing attachment 5 are brought together in a mixing chamber 51. The mixing chamber 51 has a mixing spiral in order to mix the two fluid products of the two syringes 1 with one another. At the distal end of the mixing attachment 5 a coupling part is constructed, consisting of a rotatable screw sleeve 52 and a male luer cone 53. This distally arranged coupling part of the mixing attachment 5 serves for the attaching of further attachment elements, such as for example an injection cannula or a connecting tube. The mixing attachment is described in detail in particular in the document US 2001/0004082, to which reference is to be made here.

A second embodiment of a dispensing device with an attachment part according to the invention, constructed as an attachment adapter, is shown in FIGS. 5 to 8. Identical or similar parts of the dispensing device are designated here by the same reference numbers as in the first embodiment. Differently from in the first example embodiment, an accessory is not able to be mounted here on the attachment part 3 by means of a bayonet connection, but rather the accessory is constructed as a snap-on element 6, which is able to be snapped onto the attachment structure 327 and in so doing undergoes a snap connection therewith. For this, the attachment structure 327 has two outwardly extending projections facing away from one another, which come into connection with behind-engaging elements 62 constructed on the snap-on element 6. By means of the pressing in of two pressure grips 61 lying opposite one another, the behind-engaging elements 62 of the snap-on element 6 are able to be pressed outwards away from one another, so that the snap-on element 6 is able to be separated from the attachment part 3 in a simple manner. Possible actual configurations of the attachment structure 327 are described in detail in particular in the document WO 2007/109915 and are given there the reference numbers 6, 43, 37, 120 and 220. A precise description of the snap-on element 6 is to be found in the document WO 2010/020061, wherein the snap-on element 6 is described there as an attachment piece ("Anschlussstück"). The snap-on element 6 is provided here with a spray nozzle 7. However, the mounting of any other desired attachment elements on the snap-on element 6 is conceivable, such as e.g. closure covers, mixing elements, injection cannulas etc.

Depending on the function and configuration of the accessory, it can be necessary that the outlet openings 326 of the attachment part 3 open into respectively precisely an associated inlet duct of the accessory. In this embodiment, the attachment part 3 therefore has in addition a positioning profile 328 which assists the user in the correct mounting of the snap-on element 6 on the attachment part 3. The user must mount the snap-on element 6 here on the attachment part 3 such that a positioning wing 63, projecting on one side from the plug-on element 6, is placed directly opposite the positioning element 328 (see FIG. 8). A correct mounting of the snap-on element 6 on the attachment part 3 can be ensured in addition in that the attachment structure 327 and the correspondingly complementary attachment structure of the snap-on element 6 are constructed asymmetrically with respect to the positions of the two outlet openings 326. The accessory is then only able to be attached in a possible manner on the attachment part 3.

The syringe housing, the piston 17, the syringe holder 2, the housing 32 of the attachment part 3, the rotation element 31, the connecting sleeve 4, the snap-on element 6 and the spray nozzle 7 are constructed here respectively as a whole in one piece and are produced from a plastic in an injection moulding process. However, it is also conceivable to construct the respective accessory, such as for example the mixing attachment 5 or the snap-on element 6, directly in one piece with the housing 32 of the attachment part 3. The syringe holder could also be mounted directly in one piece on two or more syringe housings.

The invention is of course not limited to the above example embodiments, and a plurality of modifications is possible. Thus, the attachment part, which does not have to be constructed as an attachment adapter, can comprise for example only one coupling part, which serves for the attaching of only one syringe 1 on the attachment part. However, more than two coupling parts can also be provided. In addition, the dispensing unit does not have to be configured as a syringe as described in the example embodiments. Any desired configuration of the dispensing unit according to the prior art is conceivable for this.

The locking structures constructed on the rotation element and on the syringe 1 do not obligatorily have to be constructed as an external or respectively internal thread, but rather can be configured in any desired manner in accordance with the prior art. It would also be possible to provide on the rotation element 31 only outwardly projecting, e.g. diametrically opposed lugs, which engage into a thread or another guide structure of the securing sleeve. In particular, for example the use of a bayonet closure is conceivable. The securing sleeve 13 could, in addition, be mounted so as to be freely rotatable on the syringe housing 11 and have a blocking function for the screwing-on, as described in US 2006/0157984. An insidious loosening of the locking between attachment part and syringe, for example in the case of vibrations, would thereby be prevented.

Furthermore, the actuating element of the rotation element 31 could be configured for example by outwardly protruding projections, instead of by a rotation ring. The rotation ring could also be mounted on the threaded sleeve 311 such that the threaded sleeve is situated spaced apart thereto radially in the interior of the rotation ring. With regard to the accessories 5 or respectively 6, a plurality of other accessories is conceivable, which can be constructed to fulfil various functions. A plurality of examples are to be found for this in the prior art.

LIST OF REFERENCE NUMBERS 1 syringe
11 housing side wall
12 holding wing
13 securing sleeve
14 male luer cone
15 delivery opening
16 reservoir
17 piston 18 pressure plate
19 sealing element
2 syringe holder
21 connecting element
22 actuating element
3 attachment part
31 rotation element
311 threaded sleeve
312 rotation ring
313 behind-engaging element
32 housing
321 attachment tube
322 female luer cone
323 shoulder
324 fluid duct
325 inlet opening
326 outlet opening
327 attachment structure
328 positioning profile
329 transverse duct
33 plug
4 connecting sleeve
5 mixing attachment
51 mixing chamber
52 screw sleeve
53 luer inner cone
6 snap-on element
61 pressure grip
62 behind-engaging element
63 positioning wing
7 spray nozzle

The invention claimed is:

1. An attachment part having a housing with at least two first coupling parts arranged parallel to one another, by means of which the attachment part is able to be attached to a dispensing unit or to a plurality of dispensing units, each of the first coupling parts having:
a female cone area with a conically constructed inner surface and with a longitudinal axis which extends centrally with respect to the inner surface, wherein the female cone area has an inlet opening going throughout the female cone area and is able to be pushed on along a pushing-on direction onto a male cone area of the dispensing unit or of the plurality of dispensing units, in order to thereby connect the attachment part with the dispensing unit or with the plurality of dispensing units, and
a rotation element, which is rotatable concentrically around the female cone area, and on which a first locking structure is formed, which is arranged in a region radially surrounding the female cone area and serves for securing the attachment part on the dispensing unit or on the plurality of dispensing units,
wherein the rotation element of each of the first coupling parts has an actuating element, which serves to rotate the rotation element relative to the female cone area,
wherein in the region of the female cone area of each of the first coupling parts a shoulder is formed with a first stop surface which points in a substantially opposite direction to the pushing-on direction,
wherein the rotation element of each of the first coupling parts has at least one behind-engaging element, which has a second stop surface pointing in the pushing on direction and abuts with the second stop surface against the first stop surface such that the first stop surface prevents a further movement of the rotation element in the pushing on direction,
wherein an oblique surface is constructed at a free end of each of the behind-engaging elements, which is inclined such with respect to the longitudinal axis of the female cone area that the oblique surface moves away from the longitudinal axis of the female cone area in the direction pointing contrary to the pushing-on direction,
wherein the rotation element of each of the first coupling parts has a rotation sleeve, on an outer side of which the locking structure is formed, and
wherein the actuating element of each of the first coupling parts is formed as a rotation ring mounted on the rotation sleeve, the at least one behind-engaging element of each of the first coupling parts being constructed in a radial inner region of the rotation ring.

2. The attachment part according to claim 1, each of the first coupling parts having an outlet opening, which is in fluid-communicating connection with one of the inlet openings of the first coupling parts, and a first attachment structure, which is suited to attach an accessory on the attachment part such that the outlet opening of each of the first coupling parts opens in a fluid-tight manner into an opposite fluid duct of the accessory.

3. The attachment part according to claim 1, wherein the female cone area of each of the first coupling parts forms a luer cone.

4. The attachment part according to claim 1, wherein the rotation element of each of the first coupling parts is freely rotatable.

5. The attachment part according to claim 1, wherein the first locking structure of each of the first coupling parts is constructed as an external thread.

6. The attachment part according to claim 1, wherein the rotation ring of each of the first coupling parts is mounted on the rotation sleeve over a connecting region extending outwards perpendicularly in radial direction.

7. The attachment part according to claim 1, wherein the rotation ring of each of the first coupling parts has a greater outside radius than the rotation sleeve.

8. The attachment part according to claim 1, wherein each of the rotation elements has at least two behind-engaging elements, which are each constructed so as to be flexible in order to enable a facilitated mounting of the rotation element on the female cone area of each of the first coupling parts,
wherein each of the at least two behind-engaging elements has a free end with which it extends in the direction substantially opposite to the pushing-on direction, the free end of each behind-engaging element having a second stop surface pointing in the pushing-on direction, and
wherein each of the behind-engaging elements abuts with the second stop surface of its free end against the first stop surface such that the first stop surface prevents a further movement of the rotation element in the pushing-on direction.

9. The attachment part according to claim 8, wherein respectively two of the behind-engaging elements form a pair lying diametrically opposite.

10. The attachment part according to claim 1, wherein the at least one behind-engaging element of each of the first coupling parts extends equally far in the opposite direction to the pushing-on direction as the rotation ring.

11. The attachment part according to claim 1, wherein the rotation element is movable along the pushing-on direction relative to the female cone area of each of the first coupling parts in an assembled state of the attachment part.

12. A dispensing device having an attachment part and a dispensing unit or a plurality of dispensing units, the attachment part having a first housing with at least two first coupling parts arranged parallel to one another, by means of which the attachment part is able to be attached to the dispensing unit or to the plurality of dispensing units, each of the first coupling parts having
- a female cone area with a conically constructed inner surface and with a longitudinal axis which extends centrally with respect to the inner surface, wherein the female cone area has an inlet opening going throughout the female cone area and is able to be pushed on along a pushing-on direction onto a male cone area of the dispensing unit or of the plurality of dispensing units, in order to thereby connect the attachment part with the dispensing unit or with the plurality of dispensing units, and
- a rotation element, which is rotatable concentrically around the female cone area, and on which a first locking structure is formed, which is arranged in a region radially surrounding the female cone area and serves for securing the attachment part on the dispensing unit or on the plurality of dispensing units,
- wherein the rotation element of each of the first coupling parts has an actuating element, which serves to rotate the rotation element relative to the female cone area,
- wherein in the region of the female cone area of each of the first coupling parts, a shoulder is formed with a first stop surface which points in a substantially opposite direction to the pushing-on direction,
- wherein the rotation element of each of the first coupling parts has at least one behind-engaging element, which has a second stop surface pointing in the pushing on direction and abuts with the second stop surface against the first stop surface such that the first stop surface prevents a further movement of the rotation element in the pushing on direction,
- wherein an oblique surface is constructed at a free end of each of the behind-engaging elements, which is inclined such with respect to the longitudinal axis of the female cone area that the oblique surface moves away from the longitudinal axis of the female cone area in the direction pointing contrary to the pushing-on direction,
- wherein the rotation element of each of the first coupling parts has a rotation sleeve, on an outer side of which the locking structure is formed,
- wherein the actuating element of each of the first coupling parts is formed as a rotation ring mounted on the rotation sleeve, the at least one behind-engaging element of each of the first coupling parts being constructed in a radial inner region of the rotation ring,
- wherein the dispensing unit or each of the plurality of dispensing units has a second housing with a reservoir, and at least two second coupling parts each of which having a securing sleeve and the male cone area, which is arranged radially at a distance within the securing sleeve and an outlet opening, which goes throughout the male cone area, and which is in fluid-communicating connection with the reservoir,
- wherein each of the female cone areas of the attachment part is able to be pushed onto one of the male cone areas of the dispensing unit or of the plurality of dispensing units, so that the reservoir is in fluid-communicating connection with the inlet openings, and
- wherein each of the securing sleeves has a second locking structure, which is able to be locked with one of the first locking structures such that the attachment part is secured on the dispensing unit or on the plurality of dispensing units.

13. The dispensing device according to claim 12, wherein each of the securing sleeves is mounted in a torque-proof manner on the second housing.

14. The dispensing device according to claim 12, wherein the dispensing unit is constructed as a double- or multiple piston syringe with at the least two second coupling parts arranged in parallel, wherein each of the first coupling parts is able to be coupled and locked with respectively one of the second coupling parts of the dispensing unit.

15. The dispensing device according to claim 14, wherein the double- or multiple piston syringe has two or more single piston syringes which are detachable from one another and are able to be used separately from one another.

16. The dispensing device according to claim 14, wherein the attachment part has a first attachment structure and several outlet openings, which are each in fluid-communicating connection with one of the inlet openings, wherein in addition the dispensing device has a mixing attachment with a second attachment structure and with a mixing chamber, and wherein the mixing attachment is able to be attached to the attachment part by connecting the first attachment structure with the second attachment structure such that the outlet openings of the attachment part are respectively in fluid-communicating connection with the mixing chamber.

17. An attachment part having a housing with at least two first coupling parts arranged parallel to one another, by means of which the attachment part is able to be attached to a dispensing unit or to a plurality of dispensing units, each of the first coupling parts having:
- a female cone area, which has an inlet opening going throughout the female cone area and which is able to be pushed on along a pushing-on direction onto a male cone area of the dispensing unit or of the plurality of dispensing units, in order to thereby connect the attachment part with the dispensing unit or with the plurality of dispensing units, and
- a rotation element, which is rotatable concentrically around the female cone area, and on which a first locking structure is formed, which is arranged in a region radially surrounding the female cone area and serves for securing the attachment part on the dispensing unit or on the plurality of dispensing units,
- wherein the rotation element of each of the first coupling parts has an actuating element, which serves to rotate the rotation element relative to the female cone area,
- wherein in the region of the female cone area of each of the first coupling parts, a shoulder is formed with a first stop surface which points in a substantially opposite direction to the pushing-on direction,
- wherein the rotation element of each of the first coupling parts has at least one behind-engaging element, which has a second stop surface pointing in the pushing on direction and abuts with the second stop surface against the first stop surface such that the first stop surface prevents a further movement of the rotation element in the pushing on direction,
- wherein the rotation element of each of the first coupling parts has a rotation sleeve, on an outer side of which the locking structure is formed,
- wherein the actuating element of each of the first coupling parts is formed as a rotation ring mounted on the rotation sleeve, the at least one behind-engaging element of each of the first coupling parts being constructed in a radial inner region of the rotation ring, and wherein the rotation element is movable along the pushing-on direction relative to the female cone area of each of the first coupling parts in an assembled state of the attachment part.

\* \* \* \* \*